United States Patent

Tsoi et al.

Patent Number: 5,958,664
Date of Patent: Sep. 28, 1999

[54] COUPLER CAPABLE OF RELEASING A DEVELOPMENT ACCELERATOR

[75] Inventors: Siu-Chung Tsoi, Watford; Peter J. Twist, Gt. Missenden, both of United Kingdom; David T. Southby, Rochester, N.Y.

[73] Assignee: Eastman Kodak Company, Rochester, N.Y.

[21] Appl. No.: 09/126,304

[22] Filed: Jul. 30, 1998

[30] Foreign Application Priority Data

Aug. 6, 1997 [GB] United Kingdom ............... 9716555

[51] Int. Cl.$^6$ ........................................ G03C 1/73
[52] U.S. Cl. .................. 430/555; 430/376; 430/554
[58] Field of Search ........................ 430/554, 555

[56] References Cited

U.S. PATENT DOCUMENTS

| | | | |
|---|---|---|---|
| 4,859,578 | 8/1989 | Michno et al. | 430/544 |
| 4,861,701 | 8/1989 | Burns et al. | 430/543 |
| 4,912,025 | 3/1990 | Platt et al. | 430/544 |
| 5,264,335 | 11/1993 | Twist et al. | 430/543 |
| 5,605,786 | 2/1997 | Saito et al. | 430/553 |

FOREIGN PATENT DOCUMENTS

| | | |
|---|---|---|
| 0 200 878 | 11/1986 | European Pat. Off. . |
| 0 347 849 | 12/1989 | European Pat. Off. . |
| 118 087 | 7/1990 | European Pat. Off. . |
| 0 495 477 | 7/1992 | European Pat. Off. . |
| 0 364 280 | 4/1995 | European Pat. Off. . |
| 0 679 943 | 11/1995 | European Pat. Off. . |
| 0 449 340 | 10/1996 | European Pat. Off. . |
| 3209110 | 7/1988 | Germany . |
| 59-197037 | 11/1984 | Japan . |

OTHER PUBLICATIONS

Japanese Patent Abstract 3107146.
Japanese Patent Abstract 1223453.
Japanese Patent Abstract 62168145.
Japanese Patent Abstract 62166340.
Japanese Patent Abstract 63259555.
Japanese Patent Abstract 63261362.
Japanese Patent Abstract 62293243.
East German Patent Abstract DD 263 146.

*Primary Examiner*—Hoa Van Le
*Attorney, Agent, or Firm*—Sarah Meeks Roberts

[57] ABSTRACT

The present invention relates to a new coupler which is capable of releasing a development accelerator having the formula:

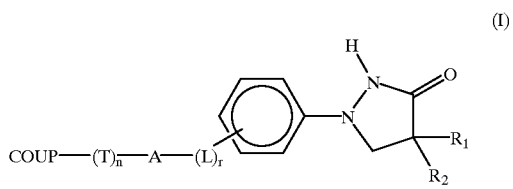

wherein
  COUP is a coupler moiety,
  T is a timing group and n is 0, 1 or 2,
  A is a group capable of being adsorbed to the silver halide surface,
  L is a linking group and r is 0 or 1, and
  $R_1$ and $R_2$ are independently selected from an alkyl group, substituted or unsubstituted, and an aryl group, substituted or unsubstituted.

The present invention also concerns a photographic silver halide recording material containing such a coupler and further relates to a process for processing such a material.

The invention provides a new DARC compound showing improved speed increase without undue fog formation.

13 Claims, 3 Drawing Sheets

COUPLER CAPABLE OF RELEASING A DEVELOPMENT ACCELERATOR

FIELD OF THE INVENTION

The present invention relates to a new coupler which is capable of releasing a development accelerator. The present invention concerns a photographic silver halide recording material containing such a coupler and, also a process for processing such a material.

BACKGROUND OF THE INVENTION

Couplers which release a development accelerator (DARC) have been described. They are added to silver halide emulsions in order to achieve an increase in speed or contrast brought about by the increased image development caused by the image-wise release of the development accelerator Typically, these couplers release a hydrazide nucleator which is activated by oxidized color developing agent and hydroxyl ions.

UK Application No. 9716554.2, filed Aug. 6, 1997, discloses a new fogging photographic processing solution for a reversal process comprising a 1-phenyl-3-pyrazolidinone derivative and a bi-nucleophilic agent.

PROBLEM TO BE SOLVED BY THE INVENTION

The above-described DARCs tend to cause fogging, however, and this limits the extent to which speed can be increased.

It is one of the objects of the present invention to provide a new DARC compound showing improved speed increase without undue fog formation.

It is a second object of the invention to provide a color photographic recording material, to be processed in the presence of a bi-nucleophilic agent, comprising a support bearing a photosensitive silver halide emulsion layer containing a coupler capable of releasing a development accelerator on color development.

Another object of the present invention is to provide a process for processing an image-wise exposed photographic material containing the new DARC compound.

SUMMARY OF THE INVENTION

According to the present invention there is provided a compound having the following formula:

(I)

wherein
COUP is a coupler moiety,
T is a timing group and n is 0, 1 or 2,
A is a group capable of being adsorbed to the silver halide surface,
L is a linking group and r is 0 or 1, and
$R_1$ and $R_2$ are independently selected from an alkyl group, substituted or unsubstituted, and an aryl group, substituted or unsubstituted.

The present invention further provides a photographic material comprising a support bearing at least one photosensitive silver halide emulsion layer and a coupler capable of releasing a development accelerator on color development in the presence of a bi-nucleophilic agent, characterized in that said material comprises a coupler capable of releasing a development accelerator having the formula as above defined.

The present invention also provides a process for processing an image-wise exposed photographic material containing a coupler capable of releasing a development accelerator as above defined wherein said photographic material is processed in a color developing solution containing a color developer and a bi-nucleophilic agent.

ADVANTAGEOUS EFFECT OF THE INVENTION

The DARC compounds of the present invention, in the presence of a bi-nucleophilic compound, allow a speed and contrast increase without undue fog formation.

BRIEF DESCRIPTION OF THE DRAWINGS

For a better understanding of the present invention, reference will now be made, by way of example only, to the accompanying drawings in which.

DETAILED DESCRIPTION OF THE INVENTION

According to the present invention, $R_1$ and $R_2$ of the above formula may independently be an alkyl group having from 1 to 12 carbon atoms, which may be substituted or unsubstituted. The alkyl groups include straight or branched chain unsaturated or saturated alkyl groups or cycloalkyl groups. According to a preferred embodiment, $R_1$ and $R_2$ are independently an alkyl group having from 1 to 4 carbon atoms.

As substituents of the alkyl groups, a large number of substituent groups can be contemplated. For example, the substituent can be hydroxy, alkoxy, carboxy, amino, amido, carbamoyl, sulphonamido or sulphamoyl, each of these being capable of further substitution, for example, with an alkyl group.

The alkyl groups can be for example methyl, ethyl, propyl, especially methyl or ethyl.

Alternatively $R_1$ and $R_2$ may independently be an aryl group, especially a phenyl group, optionally substituted in particular by one or more halogen, alkyl or alkoxy groups.

The group A capable of being adsorbed to the silver halide surface defines a group well known in the photographic field For example, A can be selected from thioureas, triazoles, benzotriazoles, mercaptotetrazoles, mercaptoimidazoles, mercaptothiazoles, mercaptooxazoles, mercaptotriazoles, indazoles, imidazoles, benzimidazoles and thioethers. According to one embodiment, A is a benzotriazole group.

The linking group L can be alkylene, —CO—, —CO—O, —O—CO, —CONR—, —NRC0—, —SO$_2$NR—, —NRSO$_2$—, where R=H, alkyl or aryl; —O—, or —O—(CH$_2$)$_n$—O— or —O—(CH$_2$)$_n$—O—CO—, where n=1–5.

According to a specific embodiment, L is in particular the group —O—CO—, linked via the oxygen atom to the phenyl group in formula (I), the linking group being hydrolyzable when released from the coupler moiety resulting in the deactivation of the nucleus after a period of time, for example after from about 15 secs. to about 1 hour, i.e. it self-destructs.

The timing group T can be any group which can be used to speed or slow the release of a photographically useful group (PUG). Two timing groups may be used in circumstances where staged release is required. Exemplary timing groups include those shown below.

The coupler moiety COUP from which the developing accelerator moiety is released can be in the present invention any moiety of known couplers wherein COUP is bonded to the released moiety in the coupling-off position.

The coupler moieties capable by reaction with oxidized developing agent of releasing a photographically useful group are particularly well known in development accelerator technology. Typically, the coupler moiety (COUP) from which the development accelerator moiety is released includes a coupler moiety employed in conventional color-forming photographic processes which yield colored products based on reaction of couplers with oxidized color developing agents. The coupler moiety can yield colorless products, or colored products that can be washed out to remove any retained color, on reaction with oxidized color developing agents.

The COUP can be unballasted or ballasted with an oil-soluble or lipophilic group.

The coupler moiety can be a magenta, yellow, cyan or universal coupler.

Magenta couplers are described in such representative patents and publications as: U.S. Pat. Nos. 2,311,082, 2,343,703, 2,369,489, 2,600,788, 2,908,573, 3,062,653, 3,152,896, 3,519,429, and "Farbkuppler-eine LiteratureUbersicht," published in Agfa Mitteilungen, Band III, pp. 126–156 (1961). Preferably such couplers are pyrazolones, pyrazolotriazoles or pyrazolobenzimidazoles.

Cyan couplers are described in such representative patents and publications as: U.S. Pat. Nos. 2,367,531, 2,423,730, 2,474,293, 2,772,162, 2,895,826, 3,002,836, 3,034,892, 3,041,236, 4,333,999, 4,883,746 and "Farbkuppler-eine LiteratureUbersicht," published in Agfa Mitteilungen, Band III, pp. 156–175 (1961). Preferably such couplers are phenols and naphthols.

Yellow couplers are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine LiteratureUbersicht," published in Agfa Mitteilungen, Band III, pp. r12–126 (1961). Such couplers are typically open chain ketomethylene compounds.

Couplers that form colorless products upon reaction with oxidized color developing agent are described in such representative patents as: British Pat. No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

According to the present invention, the DARC coupler gives a dye on reaction with oxidized color developing agent at the coupling-off position, the thus released moiety forming in the presence of a binucleophilic agent a development accelerator.

In the scope of the present invention, a bi-nucleophilic agent is an agent which comprises two active nucleophilic sites. A bi-nucleophilic agent is for example hydroxylamine, hydrogen peroxide, hydrazine or a substituted hydrazine. According to a preferred embodiment, the bi-nucleophilic agent is hydroxylamine. Indeed, hydroxylamine is generally already present in the developing solution in order to prevent oxidation of the solution, As already known in the art, a change of the amount of hydroxylamine in the developing solution tends to provide sensitometric variability. It has been unexpectedly noticed that the use of the DARC of the present invention lowers the sensitometric variability.

The bi-nucleophilic agent can be present either in the photographic material or in the developing solution. When present in the photographic material, the amount of the bi-nucleophilic agent is from 0.1 to 10 g/m$^2$, preferably from 1 to 3 g/m$^2$. The bi-nucleophilic agent can be present either in the same layer as the DARC compound or in a different layer.

When the bi-nucleophilic agent is present in the developing solution, the useful amount is from 0.1 to 20 g/l, preferably from 1 to 4 g/l.

The coating weight of a DARC in the photographic material is from 0.005 g/m$^2$ to 0.5 g/m$^2$, preferably 0.01 g/m$^2$ to 0.1 g/m$^2$.

The photographic material of the present invention will normally also contain a conventional image-dye forming coupler in addition to the DARC.

The DARC compounds of the present invention and, when present, the conventional coupler compound can be incorporated in silver halide emulsions and the emulsions can be coated on a support to form a photographic recording material. Alternatively, one or more DARC compounds and conventional couplers can be incorporated in photographic layers adjacent to the silver halide emulsion where, during development, the DARC compounds and coupler(s) will be in reactive association with the oxidized color developing agent and bi-nucleophilic agent.

The photographic elements can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of a least one red-sensitive silver halide emulsion layer having associated therewith at least one cyan dye-forming coupler, a magenta dye image-forming unit comprising at least one green sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference will be made to Research Disclosure Item 36544, September 1994, published by Kenneth Mason Publications, Emsworth, Hants PO10 7DQ, United Kingdom which will be identified hereafter by the term "Research Disclosure".

The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-β-(methanesulphonamido)ethylaniline sulphate hydrate, 4-amino-3-methyl-N-ethyl-N-β-hydroxyethylaniline sulphate, 4-amino-3-β- (methanesulphonamido)ethyl-N,N-diethylaniline hydrochloride and 4-amino-N-ethyl-N-(2-methoxyethyl)-m-toluidine di-p-toluene sulphate. With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable Alternatively, a direct positive emulsion can be employed to obtain a positive image.

Development is followed by the conventional steps of bleaching, fixing, or bleach-fixing, to remove silver and silver halide, washing and drying.

Examples of compounds within formula (I) include the following:

D1

D2

D3

D4

D5

D6

-continued

D7

D8

The following Examples are given for a better understanding of the invention.

Example 1 (Invention)

The basic developer formula used is as follows:

| Developer Composition | |
|---|---|
| Potassium carbonate (anhydrous) | 37.5 g/l |
| Sodium sulphite (anhydrous) | 4.25 g/l |
| Potassium iodide | 1.2 mg/l |
| Sodium bromide | 1.3 g/l |
| Hydroxylamine sulphate | 2.5 g/l |
| Anti-calcium agent | 6.5 ml/l |
| Color developing agent | 4.5 g/l |
| pH | 10.00 | where the anti-calcium agent is a 40% w/w aqueous solution of the penta sodium salt of diethylene triamine penta-acetic acid and the color developing agent is 4-amino-3-methyl-N-ethyl N-β-(hydroxyethyl)-aniline sulphate.

The control film was a film strip of a color negative coating comprising a support consisting of cellulose acetate and a coating structure as shown in the following diagram, with no incorporated D1:

| Coating structure | |
|---|---|
| | super-coat gelatin (1.0 g/m$^2$) |
| Gelatin (2.2 g/m$^2$) | Yellow Image Coupler (0.6 g/m$^2$) |
| Silver Halide (1.0 g/m$^2$) | D1 (0 or 0.005 g/m$^2$) |
| ////////////////////////////////////////// | |
| | Cellulose Acetate Support | where the silver halide is a 25ASA cubic iodo-bromide emulsion with 4% iodide.

The film strip according to the present invention was obtained from the film strip above described wherein the DARC compound D1 was incorporated into the color negative film above described at a coating level of 0.05 g/m$^2$.

Figure 1:
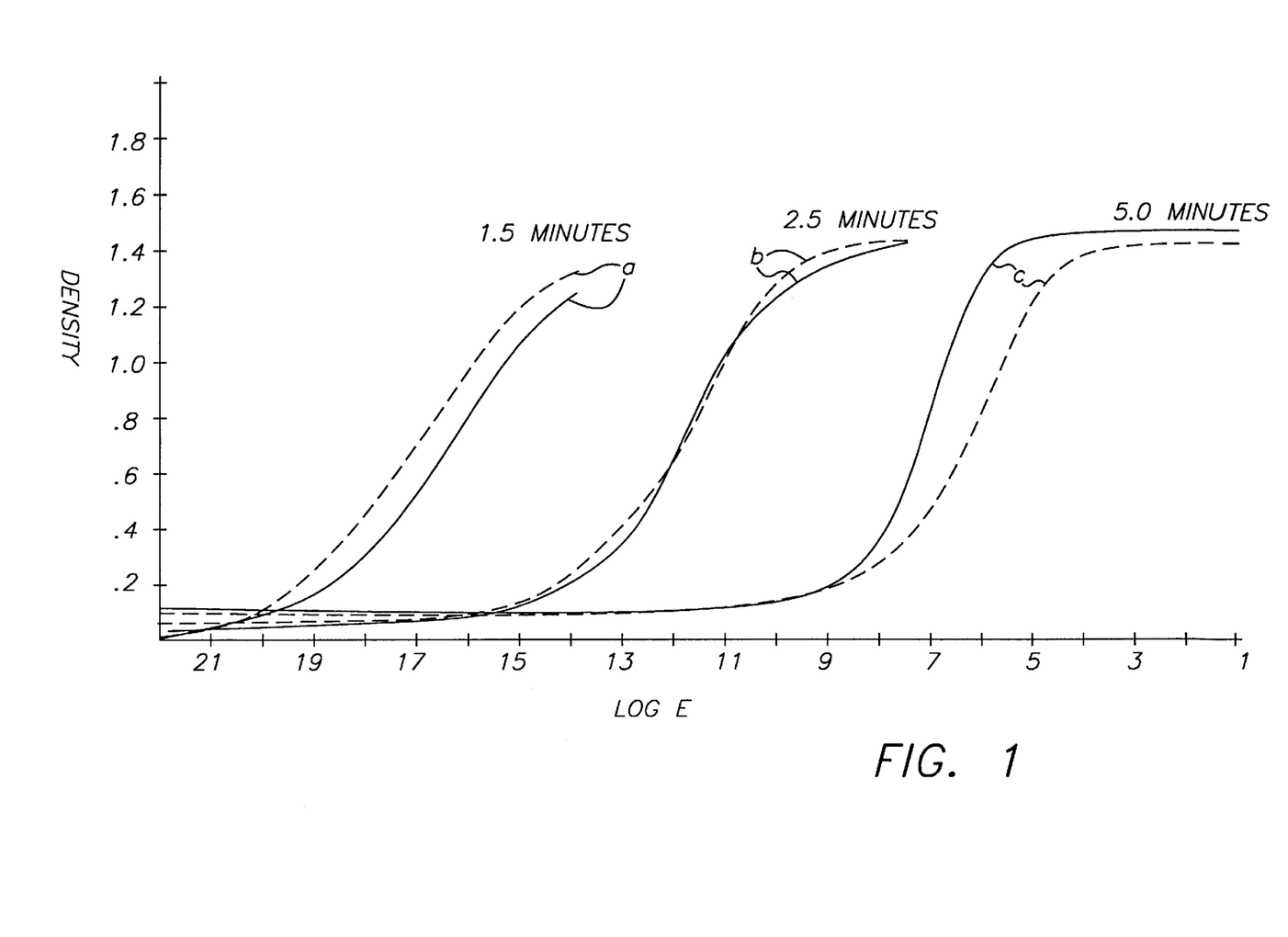
FIG. 1 is a graph which illustrates the sensitometric results obtained from Example 1.

The film strips were processed in the above described developer composition. A time-of-development series was run for 1.5, 2.5 and 5.0 minutes, represented by curves a, b and c respectively.

The results shown in FIG. 1 were obtained wherein the control film is shown by the dashed line and the film incorporating D1 is shown by the solid line.

Here it can be seen from that figure that at short development times, e.g. 1.5 minutes, the film strips with the incorporated D1 was slightly less active than the one without. As the development time was increased beyond 2.5 minutes, however, to e.g. 5 minutes, the film strip with incorporated D1 was more active and showed increased contrast and photographic speed compared to the control film strip.

This result demonstrates the development accelerator behavior of the DARC of the present invention in the presence of hydroxylamine in the color developer solution.

Example 2 (Comparison)

In this example, the two film strips of Example 1 were processed in the above described composition, omitting however the hydroxylamine.

Figure 2:
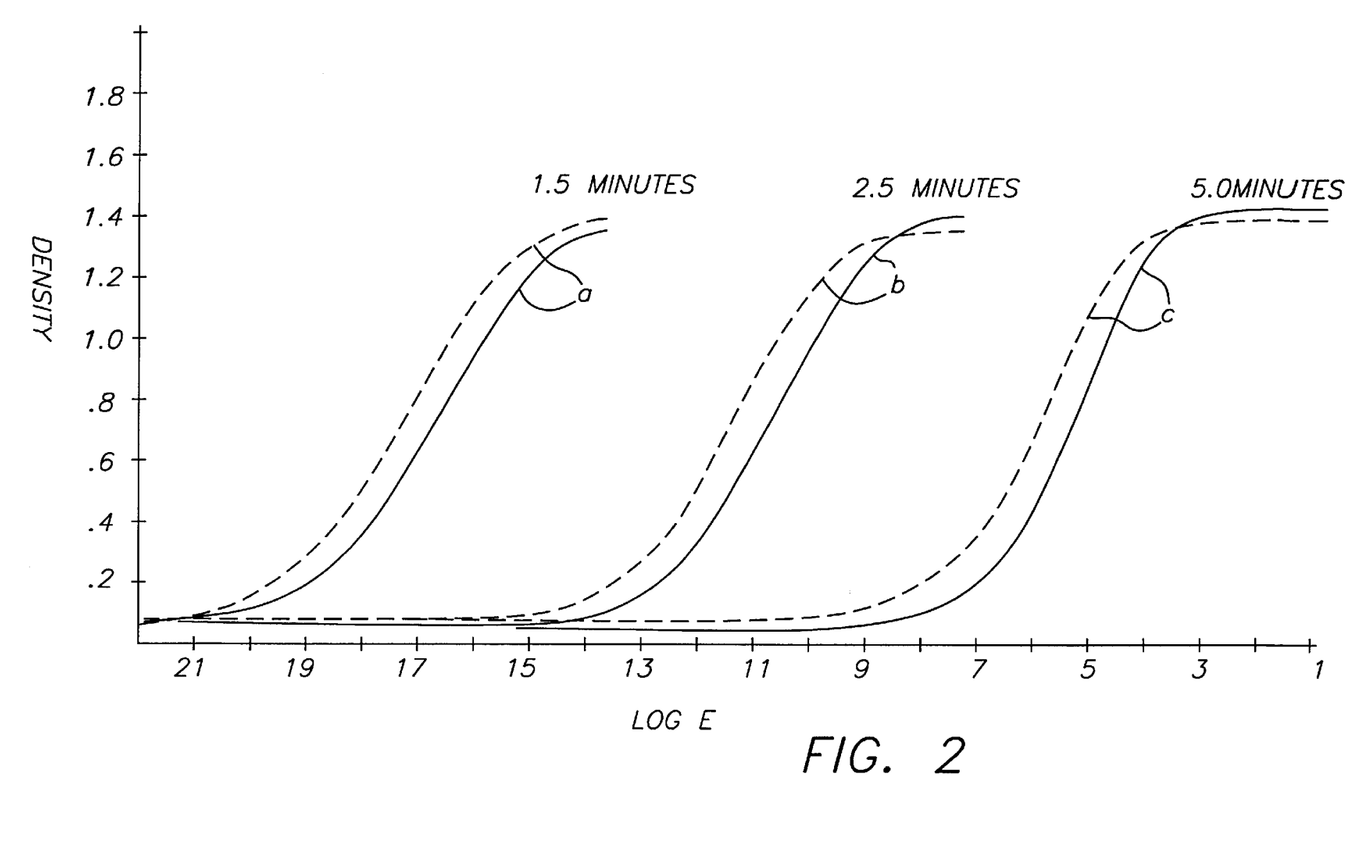
FIG. 2 is a graph which illustrates the sensitometric results obtained from Example 2.

The results are shown in FIG. 2, the dashed and solid lines representing the same as in Example 1.

It can be seen from these results that the film strip with the incorporated D1 was slightly less active than the one without D1, even at longer development times.

This result demonstrates that in the absence of hydroxylamine the effect of D1 was to cause a slight inhibition.

Example 3 (Invention)

Figure 3:
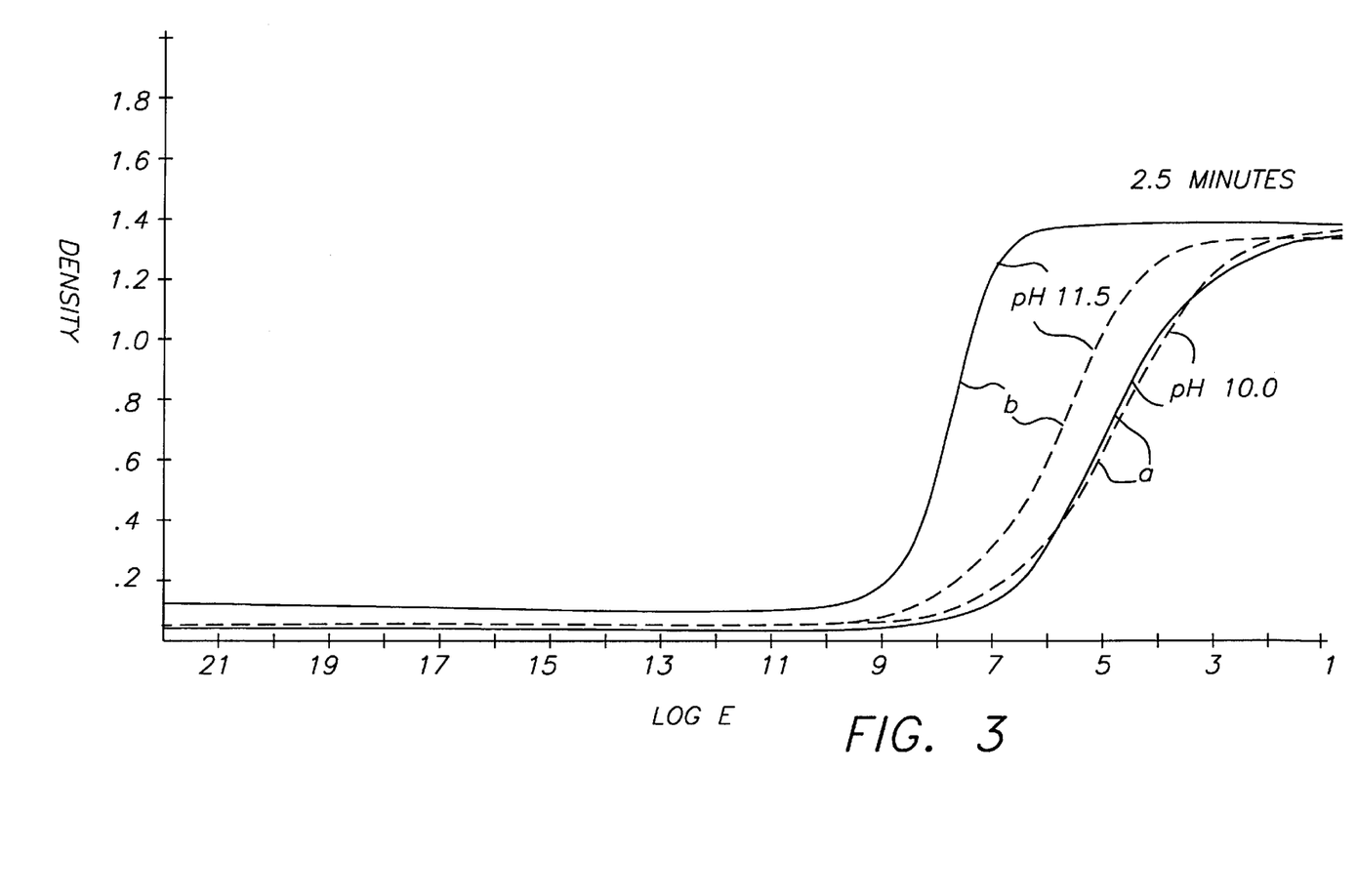
FIG. 3 is a graph which illustrates the sensitometric results is obtained from Example 3.

In this example, the film strip of Example 1 was now processed in the same developer solution including hydroxylamine for a 2.5 minute development time at two different pH levels, namely 10 and 1 1.5, represented by curves a and b respectively.

The result shown in FIG. 3 was obtained, the dashed and solid lines representing the same as in Example 1. It can be seen that although the film strip which did not contain D1 was accelerated at the higher pH, as would be expected, the film strip with incorporated D1 was unexpectedly more accelerated, giving a higher speed and contrast.

Example 4 (Synthesis of D1)

The DARC compound D1 was prepared as follows:

The compound N1 having the structure below was prepared according to the method described in published European patent application EP-A-O 449 340, using 5-aminobenzotriazole instead of 1-(3-aminophenyl)-5-mercaptotetrazole in the final stage.

N1

To a solution of N1 (4.36 g, 12.46 mmol) in dry DMF (60 ml) was added 1,1,3,3-tetramethylguanidine (1.6 g, 13.38 mmol) at room temperature under nitrogen with stirring. A solution of the chloro-coupler, C1 (6.28 g, 12.57 mmol), in dry DMF (30 ml) was then added dropwise to the above mixture over a period of 1 h. After stirring at room temperature for 5 h, the reaction mixture was poured into a rapidly stirred mixture of concentrated HCl (20 ml) and ice/water (1.25 ). The white precipitate formed was collected by filtration under suction.

After washing with water, the crude material was dried in vacuo over $P_2O_5$ at 40° C. to give a tan colored solid (10.2 g). Further purification by column chromatography gave a glassy material (4.9 g) which was dissolved in a small amount of THF and added dropwise to petrol (60–80° C.) with rapid stirring.

The precipitate was collected by filtration under suction and then dried in vacuo at 40° C. to give the product as a white solid. Yield: 4.22 g (41%). $C_{44}H_{56}ClN_7O_6$ requires: C: 64.89; H: 6.93; N:12.04% found: C: 64.61; H: 6.74; N: 11.96.

Example 5 (Synthesis of D2–D8)

The DARC compounds D2–D8 were prepared analogously by combining the appropriate coupler and coupling-off moiety by methods known in the art, such as exemplified above.

We claim:

1. A photographic material comprising a support bearing at least one photosensitive silver halide emulsion layer and a coupler capable of releasing a development accelerator on color development in the presence of a bi-nucleophilic agent, characterized in that said material comprises a coupler capable of releasing a development accelerator represented by formula (I)

(I)

wherein

COUP is a coupler moiety,

T is a timing group and n is 0, 1 or 2,

A is a group capable of being adsorbed to the silver halide surface,

L is a linking group and r is 0 or 1, and $R_1$ and $R_2$ are independently selected from an alkyl group, substituted or unsubstituted, and an aryl group, substituted or unsubstituted.

2. A photographic material according to claim 1 wherein the bi-nucleophilic agent is selected from hydroxylamine and hydrogen peroxide.

3. A photographic material according to claim 2 wherein the amount of the bi-nucleophilic agent in the photographic material is from 0.1 to 10 g/m².

4. A photographic material according to claim 1 wherein the amount of coupler in the photographic material is from 0.005 g/m² to 0.5 g/m².

5. A photographic material according to claim 1 wherein $R_1$ and $R_2$ are independently an alkyl group having from 1 to 12 carbon atoms, substituted or unsubstituted.

6. A photographic material according to claim 1 wherein A is selected from thioureas, triazoles, benzotriazoles, mercaptotetrazoles, mercaptoimidazoles, mercaptothiazoles, mercaptooxazoles, mercaptotriazoles, indazoles, imidazoles, benzimidazoles and thioethers.

7. A photographic material according to claim 1 wherein L is selected from the group consisting of alkylene, —CO—, —CO—O, O—CO—, —CONR—, —NRCO—, —SO$_2$NR—, NRSO$_2$—, where R=H, alkyl or aryl; —O—, —O—(CH$_2$)$_n$—O— and —O—(CH$_2$)$_n$—O—CO—, where n=1–5.

8. A process for processing an imagewise exposed photographic material containing a coupler capable of releasing a development accelerator represented by formula (I)

(I)

wherein
COUP is a coupler moiety,
T is a timing group and n is 0, 1 or 2,
A is a group capable of being adsorbed to the silver halide surface,
L is a linking group and r is 0 or 1, and R$_1$ and R$_2$ are independently selected from an alkyl group, substituted or unsubstituted, and an aryl group, substituted or unsubstituted; and wherein the photographic material is processed in a color developing solution containing a color developer and a bi-nucleophilic agent.

9. A process according to claim 8 wherein the bi-nucleophilic agent is selected from hydroxylamine and hydrogen peroxide.

10. A process according to claim 9 wherein the amount of the bi-nucleophilic agent is from 0.1 to 20 g/l.

11. A process according to claim 8 wherein R$_1$ and R$_2$ are independently an alkyl group having from 1 to 12 carbon atoms, substituted or unsubstituted.

12. A process according to claim 8 wherein A is selected from thioureas, triazoles, benzotriazoles, mercaptotetrazoles, mercaptoimidazoles, mercaptothiazoles, mercaptooxazoles, mercaptotriazoles. indazoles, imidazoles, benzimidazoles and thioethers.

13. A process according to claim 8 wherein L is selected from the group consisting of alkylene, —CO—, —CO—O, O—CO—, —CONR—, —NRCO—, —SO$_2$NR—, NRSO$_2$—, where R=H, alkyl or aryl; —O—, —O—(CH$_2$)$_n$—O— and —O—(CH$_2$)$_n$—O—CO—, where n=1–5.

* * * * *